United States Patent
Melton

(10) Patent No.: US 9,480,431 B2
(45) Date of Patent: Nov. 1, 2016

(54) SYSTEMS AND METHODS FOR ALCOHOL CONSUMPTION MONITORING

(75) Inventor: Donald A. Melton, Boulder, CO (US)

(73) Assignee: BI Incorporated, Boulder, CO (US)

( * ) Notice: Subject to any disclaimer, the term of this patent is extended or adjusted under 35 U.S.C. 154(b) by 114 days.

(21) Appl. No.: 13/459,302

(22) Filed: Apr. 30, 2012

(65) Prior Publication Data
US 2013/0006066 A1 Jan. 3, 2013

Related U.S. Application Data

(60) Provisional application No. 61/502,254, filed on Jun. 28, 2011.

(51) Int. Cl.
| | |
|---|---|
| *G08B 23/00* | (2006.01) |
| *A61B 5/00* | (2006.01) |
| *G01N 21/31* | (2006.01) |
| *G01N 21/359* | (2014.01) |
| *A61B 5/11* | (2006.01) |

(52) U.S. Cl.
CPC ............ *A61B 5/4845* (2013.01); *A61B 5/0002* (2013.01); *A61B 5/1113* (2013.01); *A61B 5/4266* (2013.01); *G01N 21/314* (2013.01); *G01N 21/359* (2013.01)

(58) Field of Classification Search
CPC .. G08B 23/00; A61B 5/4845; A61B 5/0002; A61B 5/1113; A61B 5/4266; A61B 5/1455; A61B 5/14546; G01N 21/65; G01N 21/314; G01N 21/359; G01N 21/3504
See application file for complete search history.

(56) References Cited

U.S. PATENT DOCUMENTS

| | | | |
|---|---|---|---|
| 5,220,919 A * | 6/1993 | Phillips et al. ............... 600/345 |
| 5,899,856 A * | 5/1999 | Schoendorfer et al. ...... 600/362 |
| 6,075,444 A * | 6/2000 | Sohege et al. ................ 340/576 |
| 6,620,108 B2 * | 9/2003 | Duval et al. .................. 600/532 |
| 7,930,927 B2 | 4/2011 | Cooper et al. |
| 8,080,206 B2 * | 12/2011 | Leddy et al. .................... 422/83 |
| 8,493,219 B2 | 7/2013 | Buck et al. |
| 8,576,065 B2 | 11/2013 | Buck et al. |
| 8,629,776 B2 | 1/2014 | Buck et al. |
| 8,657,744 B2 | 2/2014 | Rompa et al. |
| 9,240,118 B2 | 1/2016 | Melton |
| 9,241,659 B2 | 1/2016 | Rompa et al. |
| 2005/0214169 A1 * | 9/2005 | Leddy .................. G01N 27/407 422/84 |
| 2006/0202837 A1 * | 9/2006 | Hawthorne et al. ........ 340/573.1 |
| 2006/0237252 A1 * | 10/2006 | Mobley et al. ............... 180/272 |
| 2009/0087920 A1 * | 4/2009 | Pettersson ............ B60K 28/066 436/132 |
| 2010/0269566 A1 * | 10/2010 | Carroll et al. ................. 73/23.3 |
| 2010/0312431 A1 * | 12/2010 | Kaschner ........................ 701/33 |
| 2011/0015873 A1 * | 1/2011 | Iiams et al. ..................... 702/24 |
| 2011/0102182 A1 * | 5/2011 | Ohya ............................ 340/576 |
| 2011/0154887 A1 | 6/2011 | Cooper et al. |
| 2011/0178420 A1 * | 7/2011 | Ridder et al. ................. 600/532 |
| 2014/0081106 A1 * | 3/2014 | Shnaper ............... A61B 5/6829 600/365 |
| 2015/0048948 A1 | 2/2015 | Buck et al. |

(Continued)

OTHER PUBLICATIONS

U.S. Appl. No. 13/919,862, filed Jun. 17, 2013, Newell et al.
U.S. Appl. No. 14/966,135, filed Dec. 11, 2015, Donald A. Melton.

*Primary Examiner* — Firmin Backer
*Assistant Examiner* — Adnan Aziz
(74) *Attorney, Agent, or Firm* — Hamilton, DeSanctis & Cha

(57) ABSTRACT

Various embodiments of the present inventions are related to monitoring physical characteristics of a monitored individual including, but not limited to, alcohol consumption by the monitored individual.

22 Claims, 7 Drawing Sheets

(56) References Cited

U.S. PATENT DOCUMENTS

| | | |
|---|---|---|
| 2015/0061864 A1 | 3/2015 | Buck et al. |
| 2015/0078622 A1 | 3/2015 | Buck et al. |
| 2015/0131085 A1 | 5/2015 | Cooper et al. |
| 2015/0228184 A1 | 8/2015 | Buck et al. |
| 2015/0279200 A1 | 10/2015 | Buck et al. |
| 2015/0327214 A1 | 11/2015 | Buck et al. |

* cited by examiner

SYSTEMS AND METHODS FOR ALCOHOL CONSUMPTION MONITORING

CROSS REFERENCE TO RELATED APPLICATION

The present application claims priority to (i.e., is a nonprovisional of) U.S. Pat. Application No. 61/502,254 entitled "Detection of Environmental Alcohol in a Transdermal Alcohol Detection Device", and filed Jun. 28, 2011 by Melton. The entirety of the aforementioned application is incorporated herein by reference for all purposes.

BACKGROUND OF THE INVENTION

The present invention is related to physical characteristic monitoring devices, and in particular to monitoring devices capable of monitoring alcohol consumption in human subjects.

Large numbers of individuals are currently housed in prisons. This represents a significant cost to society both in terms of housing expense and wasted productivity. To address this concern, house arrest systems have been developed for use by less violent offenders. This allows the less violent offender to be monitored outside of a traditional prison system and allows the offender an opportunity to work and interact to at least some degree in society. The same approach is applied to paroled prisoners allowing for a monitored transition between a prison atmosphere and returning to society.

In some cases, it is not practical to parole an offender because they suffer from an alcohol addiction that may lead to the same activity that led to their original incarceration. Present approaches to monitor alcohol consumption are costly, time consuming and in some cases, impractical. In other cases, the terms of an individual's parole may include a requirement that the individual abstain from the use of alcohol, but monitoring adherence to such terms is costly and time consuming. In yet other circumstances, it may be possible that an individual could avoid incarceration altogether if they agree to abstain from the use of alcohol. Again, assuring adherence to such terms is at best costly and time consuming.

Various remote alcohol consumption monitoring systems have been developed, but they exhibit some weaknesses. Such weaknesses limit the utility of such systems. Thus, for at least this reason, there exists a need in the art for more advanced approaches, devices and systems for detecting alcohol usage by an individual.

BRIEF SUMMARY OF THE INVENTION

The present invention is related to physical characteristic monitoring devices, and in particular to monitoring devices capable of monitoring alcohol consumption in human subjects.

Various embodiments of the present invention provide systems for alcohol monitoring. The systems include a first alcohol sensor, a second alcohol sensor, and a processor. The first alcohol sensor is operable to detect a first alcohol content at a first location. The second alcohol sensor is operable to detect a second alcohol content at a second location. The processor is operable to process both the first alcohol content and the second alcohol content to yield a drinking indication. In some instances of the aforementioned embodiments, the first alcohol sensor and the second alcohol sensor are associated with a monitor device. In such instances, the monitor device is attachable to a monitored individual. In some cases, the drinking indication corresponds to alcohol consumption of the monitored individual.

In various instances of the aforementioned embodiments, the first alcohol sensor is directed toward the skin of the monitored individual, the second alcohol sensor is directed toward an environment around the monitored individual, and the first location is nearer the monitored individual than the second location. In other instances of the aforementioned embodiments, the first alcohol sensor is directed toward the skin of the monitored individual, and the second alcohol sensor is directed toward the skin of the monitored individual. In some such instances, the system further includes a third alcohol sensor directed away from the skin of the monitored individual and operable to detect a third alcohol content. The processor is further operable to process all of the first alcohol content the second alcohol content, and the third alcohol content to yield the drinking indication. In one particular instance, processing all of the first alcohol content, the second alcohol content, and the third alcohol content to yield the drinking indication includes: subtracting the second alcohol content from the first alcohol content to yield a first composite alcohol content; and subtracting the third alcohol content from the first alcohol content to yield a second composite alcohol content.

In various instances of the aforementioned embodiments, the monitor device further includes: a location monitor circuit operable to monitor a location of the monitored individual; a tamper monitor circuit operable to monitor a tampering of the monitor device; and/or a strap operable to attach the monitor device to the monitored individual.

Other embodiments of the present invention provide methods for monitoring alcohol consumption by a monitored individual. The methods include: receiving a first alcohol content value derived from a first alcohol sensor disposed in relation to a monitored individual; receiving a second alcohol content value derived from a second alcohol sensor disposed in relation to the monitored individual; and determining alcohol consumption by the monitored individual using both the first alcohol content value and the second alcohol content value. In some cases, the first alcohol sensor and the second alcohol sensor are associated with a monitor device. In such cases, the methods may further include attaching the monitor device to the monitored individual. In particular cases, the methods further include: reporting the first alcohol content value and the second alcohol content value to a central monitor via a communication link. In other cases, the methods further include reporting the drinking indication to a central monitor via a communication link.

This summary provides only a general outline of some embodiments according to the present invention. Many other objects, features, advantages and other embodiments of the present invention will become more fully apparent from the following detailed description, the appended claims and the accompanying drawings and figures.

BRIEF DESCRIPTION OF THE DRAWINGS

A further understanding of the various embodiments of the present invention may be realized by reference to the figures which are described in remaining portions of the specification. In the figures, similar reference numerals are used throughout several drawings to refer to similar components. In some instances, a sub-label consisting of a lower case letter is associated with a reference numeral to denote one of multiple similar components. When reference is made to a reference numeral without specification to an existing sub-label, it is intended to refer to all such multiple similar components.

DETAILED DESCRIPTION OF THE INVENTION

The present invention is related to physical characteristic monitoring devices, and in particular to monitoring devices capable of monitoring alcohol consumption in human subjects.

Some embodiments of the present invention provide portable alcohol monitoring devices. Such devices include a device body and at least two alcohol sensors. As used herein, the phrase "device body" is used in its broadest sense to mean a portion of a device including hardware for performing one or more functions. In some cases, the device body may be a case holding one or more functional elements, while in other cases, the device body includes two or more cases with each holding functional elements.

In some instances of the aforementioned embodiments, the alcohol monitoring devices further include a securing device that is operable to secure the device body to the subject. In the aforementioned embodiments, the alcohol sensors may be associated with the device body, or may be associated with the securing device. In various instances of the aforementioned embodiments, at least one of the alcohol sensors is incorporated in the device body, and a force element presses the alcohol sensor toward the subject. As used herein, the phrase "force element" is used in its broadest sense to mean an element capable of providing some level of force to an object. As one example, the force element may be a spring and the alcohol sensor may be coupled to the device body via a bellows. As another example, the force element may be a torsion spring. It should be noted that while the devices, systems and methods are described herein as using alcohol sensors, that sensors capable of sensing other gases or vapors may be used in relation to other embodiments of the present invention.

Figure 1:
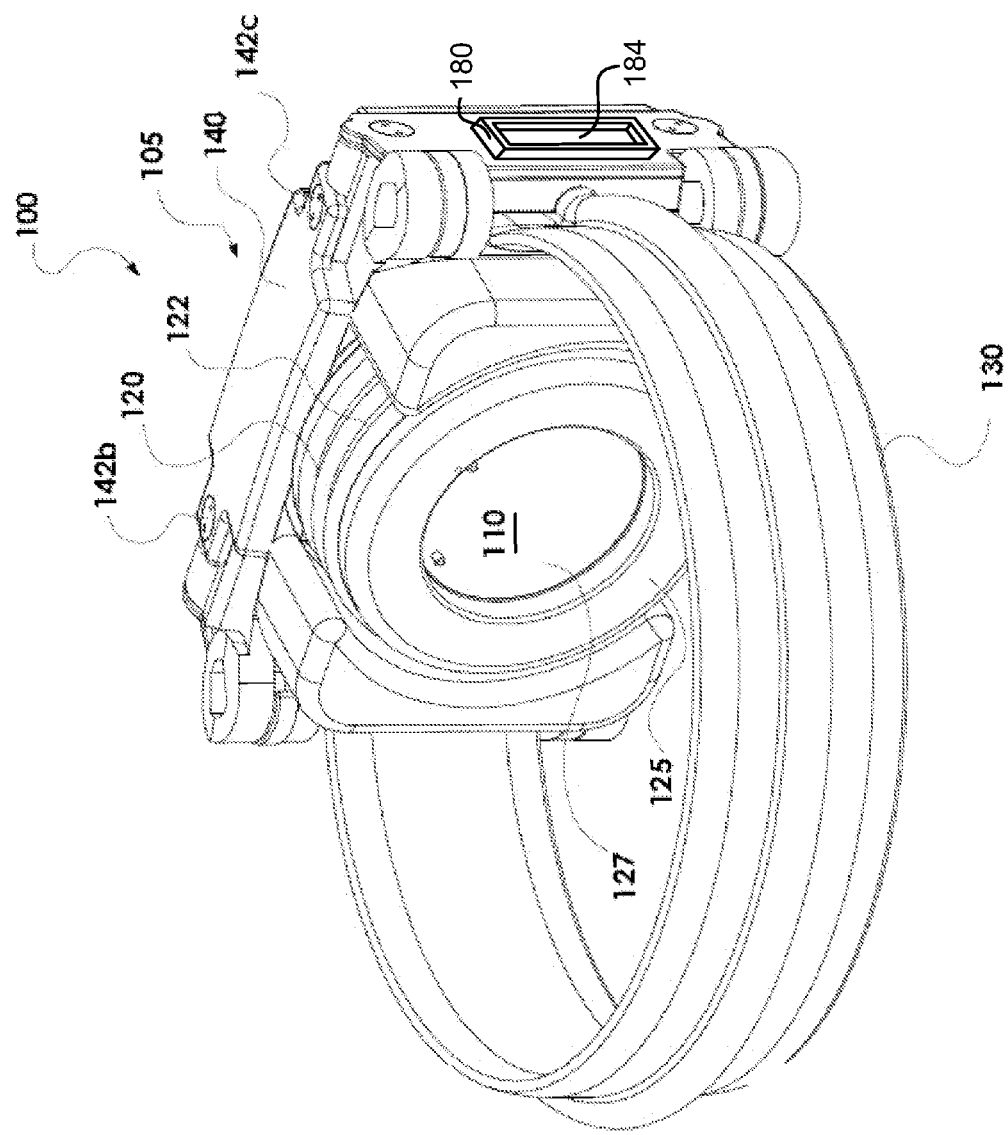
FIG. 1 depicts an alcohol monitoring device including both a transdermal alcohol monitor and an environmental alcohol monitor in accordance with various embodiments of the present invention.

Turning to FIG. 1, an alcohol monitoring device 100 is depicted that includes both a transdermal alcohol sensor 110 and an environmental alcohol sensor 184 in accordance with various embodiments of the present invention. Transdermal alcohol sensor 110 and environmental alcohol sensor 184 are each operable to detect the presence of alcohol in a gas such as air. In some embodiments of the present invention, transdermal alcohol sensor 110 and environmental alcohol sensor 184 may be the same type of sensor, or may be implemented using different types of sensors. In one particular embodiment of the present invention, both transdermal alcohol sensor 110 and environmental alcohol sensor 184 may include a fuel cell based on PEM sensor technology available from Giner Inc. of Newton, Mass., or any other alcohol detection sensor known in the art. The monitoring circuitry may include location monitoring circuitry as is known in the art, or other monitoring circuitry used to determine attributes and/or location of a monitored individual. Environmental alcohol sensor 184 is surrounded by a housing 180.

In addition, alcohol monitoring device 100 may include location monitoring circuitry and/or data transmission circuitry. The location monitoring circuitry may include, but is not limited to, global position system locating circuitry. The data transmission circuitry may include, but is not limited to, transmission and/or reception circuitry as is known in the art for transmitting information from alcohol monitoring device 100, and receiving information at alcohol monitoring device 100. The information transmitted by alcohol monitoring device may include an indication of whether a monitored individual has been consuming alcohol and to what level the consumption has progressed, and/or current and historic location information of the subject wearing alcohol monitoring device.

In addition, alcohol monitoring device 100 may include tamper circuitry. Such tamper circuitry may include any circuitry known in the art that are capable of determining whether any interference with alcohol monitoring device 100 has occurred or is ongoing. Such interference may include, but is not limited to, blocking the alcohol sensor, interfering with the transmission of information to/from alcohol monitoring device 100, and/or cutting an attachment securing alcohol monitoring device 100 to the human subject. Such tamper sensors may include, but are not limited to, a proximity sensor that is able to determine whether alcohol monitoring device 100 is within reasonable proximity of the skin of the monitored individual. Based on the disclosure provided herein, one of ordinary skill in the art will recognize a variety of tamper sensors that may be used in conjunction with the various embodiments of the present invention. The various sensors included in alcohol measurement device 100 may include, but are not limited to, a blockage sensor indicating that no gas is being allowed to reach an included alcohol sensor, a temperature sensor, a proximity sensor indicating that alcohol measurement device is within a defined range of the monitored individual, a skin probe capable of measuring skin resistance as an indication of whether alcohol measurement device is still being worn by the monitored individual, and/or the like. Based on the disclosure provided herein, one of ordinary skill in the art will recognize a variety of other sensors that may be used in relation to different embodiments of the present invention.

The aforementioned location information, alcohol information, and/or tamper information may be transmitted to a central monitoring station where it is monitored. Based on the disclosure provided herein, one of ordinary skill in the art will recognize a variety of information that may be transmitted to/from alcohol monitoring device, a variety of uses of such information, and a variety of transmission methods and protocols that may be utilized in accordance with different embodiments of the present invention. It should be noted that in some embodiments of the present invention that alcohol information may be transmitted without the other information or along with other information. In one particular embodiment of the present invention, location information is not available. In such a case, the alcohol information may be transferred to a central monitoring station via a fixed or mobile translation device. Based upon the disclosure provided herein, one of ordinary skill in the art will recognize a variety of configurations and different data transfers that may be effectuated in accordance with different embodiments of the present invention.

A body 105 is attachable to a human subject using a strap 130. Strap 130 is attachable using some sort of buckle or other connector as are known in the art. In some cases, strap 130 includes a continuity detector (not shown) imbedded therein. In one particular embodiment of the present invention, the continuity detector is an electrical conductor extending around strap 130 and making a connection in body 105. As such, when strap 130 is either unbuckled or cut, the electrical conductor is broken and the break is detected by circuitry within body 105. In other particular embodiments of the present invention, the continuity detector is a fiber optic conductor that may similarly be used to determine whether strap 130 has been unbuckled or cut. Based on the disclosure provided herein, one of ordinary skill in the art will appreciate a variety of straps and associated securing devices that may be used in accordance with different embodiments of the present invention to secure body 105 to a monitored individual. In one particular embodiment, strap 130 includes an outer case with an imbedded fiber optic continuity conductor and banding for added strength.

Body 105 includes transdermal alcohol sensor 110 that is maintained at a controlled distance from the monitored individual's skin by a dermal seal 125 and a telescoping housing 120. The combination of dermal seal 125 and telescoping housing 120 create a reasonably stable gas region 127 between alcohol sensor 110 and the monitored individual's skin. Dermal seal 125 may be, for example, a set of foam pads that are capable of creating a reasonable seal with the skin of a monitored individual, and yet are comfortable to the monitored individual. In particular instances, the foam pads are made of closed cell foam that allows for positioning and ergonomic fit. Based on the disclosure provided herein, one of ordinary skill in the art will recognize other materials that may be used to form dermal seal 125 in accordance with the various embodiments of the present invention. Telescoping housing 120 is operable to press alcohol sensor 110 near the skin of the monitored individual. Because of this, alcohol sensor 110 is maintained at a reasonably constant distance from the monitored individual's skin even when the individual is moving. This promotes better readings from alcohol sensor 110 without the need to tighten strap 130 beyond a comfortable point. As more fully described below, in one embodiment of the present invention, telescoping housing 120 includes an expandable bellows 122 that allows for movement of alcohol sensor 110 relative to body 105, and a spring (not shown) that presses transdermal alcohol sensor 110 and dermal seal 125 away from body 105 and toward the human subject's skin. In particular instances of the aforementioned embodiments, expandable bellows 122 is made of rubber, while in other instances it is formed of some type of flexible plastic. Based on the disclosure provided herein, one of ordinary skill in the art will recognize a variety of materials that may be used to create expandable bellows 122 in accordance with various embodiments of the present invention.

Body 105 also includes a water tight compartment 140 that includes a replaceable, fixed, or refillable liquid cartridge (not shown) and electronics (not shown) for operating alcohol monitoring device 100. Water tight compartment 140 is accessible by removing tamper resistant screws 142. In some embodiments of the present invention, tamper resistant screws 142 may require a special tool for removal to minimize the possibility that a monitored individual will open water tight compartment 140 and attempt to interfere or otherwise control the operation of alcohol monitoring device 100. In other embodiments of the present invention, tamper resistant screws 142 are only one way devices allowing for the closure of water tight compartment 140. Opening water tight compartment 140 requires the destruction of tamper resistant screws 142. When water tight compartment 140 is to be resealed, a new pair of tamper resistant screws is required. In this way, any unauthorized opening of water tight compartment 140 will be readily apparent. In some cases, the aforementioned approach may be combined with a sensor (not shown) that indicates that water tight compartment 140 is open. Thus, when water tight compartment 140 is opened an error message may be prepared and transmitted to a central monitoring location by alcohol monitoring device 100. This would allow for detection of any tampering within a reasonable period of when the tampering occurred, and additional scrutiny of the monitored individuals behavior during that period.

In operation, transdermal alcohol sensor 110 senses a concentration of alcohol in the gas near the subjects skin. When a level of alcohol in the area surrounding the subjects skin exceeds a defined level, information from environmental alcohol sensor 184 is used to verify that the alcohol level detected by transdermal alcohol sensor 110 is attributable to alcohol consumption of the subject and not to alcohol in the surrounding environment. In particular, environmental alcohol sensor 184 senses a concentration of alcohol in the environment around the subject. This alcohol may exist due to the use of lotion or other alcohol containing products on or near the subject being monitored.

Where environmental alcohol sensor 184 measures an insignificant concentration of alcohol in the environment around the subject, the concentration of alcohol sensed by transdermal alcohol sensor 110 is attributed to alcohol consumed by the subject. In contrast, where environmental alcohol sensor 184 measures a concentration of alcohol in the environment around the subject that is much greater than that sensed by transdermal alcohol sensor 110, the concentration of alcohol sensed by transdermal alcohol sensor 110 is attributed to the environment. As a third possibility, where environmental alcohol sensor 184 measures an concentration of alcohol in the environment around the subject that is similar to that sensed by transdermal alcohol sensor 110, at least some of the concentration of alcohol sensed by transdermal alcohol sensor 110 may be attributable to alcohol consumed by the subject and the alcohol in the environment may have been purposely placed to mask alcohol consumption by the subject. In such a situation, it may be possible to watch the relative concentrations of alcohol concentrations from transdermal alcohol sensor 110 and environmental alcohol sensor 184 over time before making a determination of alcohol consumption. As alcohol in the body dissipates more slowly than in the environment, it may be possible that the alcohol concentration sensed by transdermal alcohol sensor 110 will increase relative to that detected by environmental alcohol sensor 184 over time.

The following pseudocode represents an exemplary alcohol detection operation performed by transdermal alcohol sensor 110 and environmental alcohol sensor 184:

```
Receive Sensed Information from Transdermal Alcohol Sensor 110;
Calculate Transdermal Sensor Alcohol Concentration (TSAC);
Receive Sensed Information from Environmental Alcohol Sensor 184;
Calculate Environmental Sensor Alcohol Concentration (ESAC);
If ([TSAC−ESAC] > Differential Threshold Value){
    If (TSAC > Drinking Event Value){
        Report Subject Drinking Event
    }
}
Else If ([ESAC−TSAC] > Differential Threshold Value){
    Report Environmental Alcohol Event
}
Else {
    Continue Plotting Data to Differentiate Subject Drinking and
    Environment
}
```

It should be noted that information from environmental alcohol sensor 184 and transdermal alcohol sensor 110 may be reported separately to a central monitoring system, or may be combined and reported as a combined indicator. Alternatively the information from environmental alcohol sensor 184 and transdermal alcohol sensor 110 may be reported separately to a central monitoring system, and the information may be combined and reported as a combined indicator. Based upon the disclosure provided herein, one of ordinary skill in the art will recognize a variety of combinations of reporting information including sensed data, processed data, and/or consumption indicators that may be provided from a combination of environmental alcohol sensor 184 and transdermal alcohol sensor 110.

Figure 2:
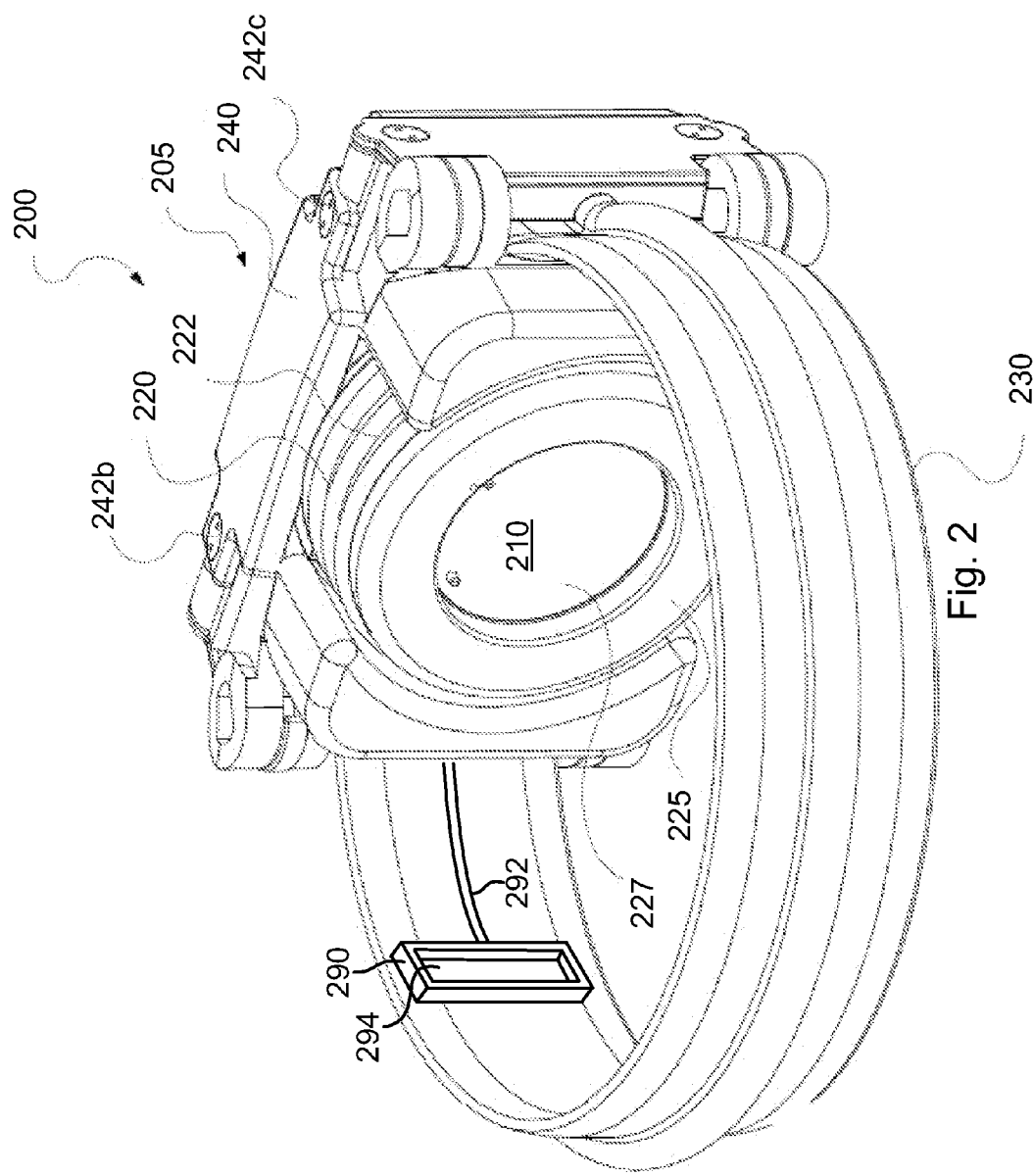
FIG. 2 depicts another alcohol monitoring device including dual transdermal alcohol monitors in accordance with various embodiments of the present invention.

Turning to FIG. 2, another alcohol monitoring device 200 is depicted that includes a first transdermal alcohol sensor 210 and a second transdermal alcohol sensor 294 in accordance with various embodiments of the present invention. Transdermal alcohol sensor 210 and transdermal alcohol sensor 294 are each operable to detect the presence of alcohol in a gas such as air. In some embodiments of the present invention, transdermal alcohol sensor 210 and transdermal alcohol sensor 294 may be the same type of sensor displaced some distance to perform a differential measurement, or may be implemented using different types of sensors. In one particular embodiment of the present invention, both transdermal alcohol sensor 210 and transdermal alcohol sensor 294 may include may include a fuel cell based on PEM sensor technology available from Giner Inc. of Newton, Mass., or any other alcohol detection sensor known in the art. The monitoring circuitry may include location monitoring circuitry as is known in the art, or other monitoring circuitry used to determine attributes and/or location of a monitored individual. Transdermal alcohol sensor 294 is surrounded by a housing 280.

In addition, alcohol monitoring device 200 may include location monitoring circuitry and/or data transmission circuitry. The location monitoring circuitry may include, but is not limited to, global position system locating circuitry. The data transmission circuitry may include, but is not limited to, transmission and/or reception circuitry as is known in the art for transmitting information from alcohol monitoring device 200, and receiving information at alcohol monitoring device 200. The information transmitted by alcohol monitoring device may include an indication of whether a monitored individual has been consuming alcohol and to what level the consumption has progressed, and/or current and historic location information of the subject wearing alcohol monitoring device.

In addition, alcohol monitoring device 200 may include tamper circuitry. Such tamper circuitry may include any circuitry known in the art that are capable of determining whether any interference with alcohol monitoring device 200 has occurred or is ongoing. Such interference may include, but is not limited to, blocking the alcohol sensor, interfering with the transmission of information to/from alcohol monitoring device 200, and/or cutting an attachment securing alcohol monitoring device 200 to the human subject. Such tamper sensors may include, but are not limited to, a proximity sensor that is able to determine whether alcohol monitoring device 200 is within reasonable proximity of the skin of the monitored individual. Based on the disclosure provided herein, one of ordinary skill in the art will recognize a variety of tamper sensors that may be used in conjunction with the various embodiments of the present invention. The various sensors included in alcohol measurement device 200 may include, but are not limited to, a blockage sensor indicating that no gas is being allowed to reach an included alcohol sensor, a temperature sensor, a proximity sensor indicating that alcohol measurement device is within a defined range of the monitored individual, a skin probe capable of measuring skin resistance as an indication of whether alcohol measurement device is still being worn by the monitored individual, and/or the like. Based on the disclosure provided herein, one of ordinary skill in the art will recognize a variety of other sensors that may be used in relation to different embodiments of the present invention.

The aforementioned location information, alcohol information, and/or tamper information may be transmitted to a central monitoring station where it is monitored. Based on the disclosure provided herein, one of ordinary skill in the art will recognize a variety of information that may be transmitted to/from alcohol monitoring device, a variety of uses of such information, and a variety of transmission methods and protocols that may be utilized in accordance with different embodiments of the present invention.

A body 205 is attachable to a human subject using a strap 230. Strap 230 is attachable using some sort of buckle or other connector as are known in the art. In some cases, strap 230 includes a continuity detector (not shown) imbedded therein. In one particular embodiment of the present invention, the continuity detector is an electrical conductor extending around strap 230 and making a connection in body 205. As such, when strap 230 is either unbuckled or cut, the electrical conductor is broken and the break is detected by circuitry within body 205. In other particular embodiments of the present invention, the continuity detector is a fiber optic conductor that may similarly be used to determine whether strap 230 has been unbuckled or cut. Based on the disclosure provided herein, one of ordinary skill in the art will appreciate a variety of straps and associated securing devices that may be used in accordance with different embodiments of the present invention to secure body 205 to a monitored individual. In one particular embodiment, strap 230 includes an outer case with an imbedded fiber optic continuity conductor and banding for added strength.

Body 205 includes transdermal alcohol sensor 210 that is maintained at a controlled distance from the monitored individual's skin by a dermal seal 225 and a telescoping housing 220. The combination of dermal seal 225 and telescoping housing 220 create a reasonably stable gas region 227 between alcohol sensor 210 and the monitored individual's skin. Dermal seal 225 may be, for example, a set of foam pads that are capable of creating a reasonable seal with the skin of a monitored individual, and yet are comfortable to the monitored individual. In particular instances, the foam pads are made of closed cell foam that allows for positioning and ergonomic fit. Based on the disclosure provided herein, one of ordinary skill in the art will recognize other materials that may be used to form dermal seal 225 in accordance with the various embodiments of the present invention. Telescoping housing 220 is operable to press alcohol sensor 210 near the skin of the monitored individual. Because of this, alcohol sensor 210 is maintained at a reasonably constant distance from the monitored individual's skin even when the individual is moving. This promotes better readings from alcohol sensor 210 without the need to tighten strap 230 beyond a comfortable point. As more fully described below, in one embodiment of the present invention, telescoping housing 220 includes an expandable bellows 222 that allows for movement of alcohol sensor 210 relative to body 205, and a spring (not shown) that presses transdermal alcohol sensor 210 and dermal seal 225 away from body 205 and toward the human subject's skin. In particular instances of the aforementioned embodiments, expandable bellows 222 is made of rubber, while in other instances it is formed of some type of flexible plastic. Based on the disclosure provided herein, one of ordinary skill in the art will recognize a variety of materials that may be used to create expandable bellows 222 in accordance with various embodiments of the present invention. In some embodiments of the present invention, housing 280 may be replaced with the same housing surrounding transdermal alcohol sensor 294 to limit the amount of environmental alcohol measured. In other embodiments of the present invention, transdermal alcohol sensor 294 is purposely not secured to the subject's skin to therefore provide more of a reading of environmental alcohol.

Body 205 also includes a water tight compartment 240 that includes a replaceable liquid cartridge (not shown) and electronics (not shown) for operating alcohol monitoring device 200. Water tight compartment 240 is accessible by removing temper resistant screws 242. In some embodiments of the present invention, tamper resistant screws 242 may require a special tool for removal to minimize the possibility that a monitored individual will open water tight compartment 240 and attempt to interfere or otherwise control the operation of alcohol monitoring device 200. In other embodiments of the present invention, tamper resistant screws 242 are only one way devices allowing for the closure of water tight compartment 240. Opening water tight compartment 240 requires the destruction of tamper resistant screws 242. When water tight compartment 240 is to be resealed, a new pair of tamper resistant screws is required. In this way, any unauthorized opening of water tight compartment 240 will be readily apparent. In some cases, the aforementioned approach may be combined with a sensor (not shown) that indicates that water tight compartment 240 is open. Thus, when water tight compartment 240 is opened an error message may be prepared and transmitted to a central monitoring location by alcohol monitoring device 200. This would allow for detection of any tampering within a reasonable period of when the tampering occurred, and additional scrutiny of the monitored individuals behavior during that period. Information sensed by transdermal alcohol sensory 294 is transmitted to the electronics in body 205 via a communication path 292. This communication path 292 may also provide any liquid necessary to operate transdermal alcohol sensor 294 from body 205.

In operation, transdermal alcohol sensor 210 senses a concentration of alcohol in the gas near the subjects skin at a first location. Where transdermal alcohol sensor 294 is sealed to the subject's skin similar to that of transdermal alcohol sensor 210 and a level of alcohol in the area surrounding the subjects skin as sensed by transdermal alcohol sensor 210 exceeds a defined level, information from transdermal alcohol sensor 294 is used to determine if the sensed alcohol concentration is localized to transdermal alcohol sensor 210 or transdermal alcohol sensor 294, or if a similar concentration is being sensed by both transdermal alcohol sensor 210 and transdermal alcohol sensor 294. Where a similar alcohol concentration is being reported by both transdermal alcohol sensory 210 and transdermal alcohol sensor 294, it is less likely that environmental alcohol is being detected. In contrast, where there is a substantial difference between the alcohol concentration reported by transdermal alcohol sensor 210 and that reported by transdermal alcohol sensor 294, it is more likely that environmental alcohol is being detected by one of the alcohol sensors.

The following pseudocode represents an exemplary alcohol detection operation performed by transdermal alcohol sensor 210 and environmental alcohol sensor 294:

```
Receive Sensed Information from Transdermal Alcohol Sensor 210;
Calculate Transdermal Sensor Alcohol Concentration (TSAC1);
Receive Sensed Information from Transdermal Alcohol Sensor 294;
Calculate Transdermal Sensor Alcohol Concentration (TSAC2);
If (absolute[TSAC1-TSAC2] <= Differential Threshold Value){
    If (TSAC1 > Drinking Event Value){
        Report Subject Drinking Event
    }
}
Else If (absolute[TSAC1-TSAC2] <= Differential Threshold Value){
    Report Possible Environmental Alcohol Event
}
```

Alternatively, where transdermal alcohol sensor 294 is not sealed to the subject's skin similar to that of transdermal alcohol sensor 210 it operates more as an environmental alcohol sensor. In such a case when a level of alcohol in the area surrounding the subjects skin exceeds a defined level as indicated by transdermal alcohol sensor 210, information from transdermal alcohol sensor 294 is used to verify that the alcohol level detected by transdermal alcohol sensor 210 is attributable to alcohol consumption of the subject and not to alcohol in the surrounding environment. In particular, transdermal alcohol sensor 294 because it is not sealed to the subject's skin is more sensitive to environmental alcohol than is transdermal alcohol sensor 294, and thus senses a concentration of alcohol in the environment around the subject. Again, such environmental alcohol may exist due to the use of lotion or other alcohol containing products on or near the subject being monitored.

Where transdermal alcohol sensor 210 measures concentrations substantially higher than transdermal alcohol sensory 294, the concentration of alcohol sensed by transdermal alcohol sensor 210 is attributed to alcohol consumed by the subject. In contrast, where transdermal alcohol sensor 210 measures an concentration of alcohol that is much less than that sensed by transdermal alcohol sensor 294, the concentration of alcohol sensed by transdermal alcohol sensor 210 is attributed to the environment.

The following pseudocode represents an exemplary alcohol detection operation performed by transdermal alcohol sensor 210 and environmental alcohol sensor 294:

```
Receive Sensed Information from Transdermal Alcohol Sensor 210;
Calculate Transdermal Sensor Alcohol Concentration (TSAC1);
Receive Sensed Information from Transdermal Alcohol Sensor 294;
Calculate Environmental Sensor Alcohol Concentration (TSAC2);
If ([TSAC1-TSAC2] > Differential Threshold Value){
    If (TSAC > Drinking Event Value){
        Report Subject Drinking Event
    }
}
Else If ([TSAC2-TSAC1] > Differential Threshold Value){
    Report Environmental Alcohol Event
}
Else {
    Continue Plotting Data to Differentiate Subject Drinking and
    Environment
}
```

It should be noted that information from transdermal alcohol sensor 294 and transdermal alcohol sensor 210 may be reported separately to a central monitoring system, or may be combined and reported as a combined indicator. Alternatively the information from transdermal alcohol sensor 294 and transdermal alcohol sensor 210 may be reported separately to a central monitoring system, and the information may be combined and reported as a combined indicator. Based upon the disclosure provided herein, one of ordinary skill in the art will recognize a variety of combinations of reporting information including sensed data, processed data, and/or consumption indicators that may be provided from a combination of environmental alcohol sensor 294 and transdermal alcohol sensor 210.

Figure 3:
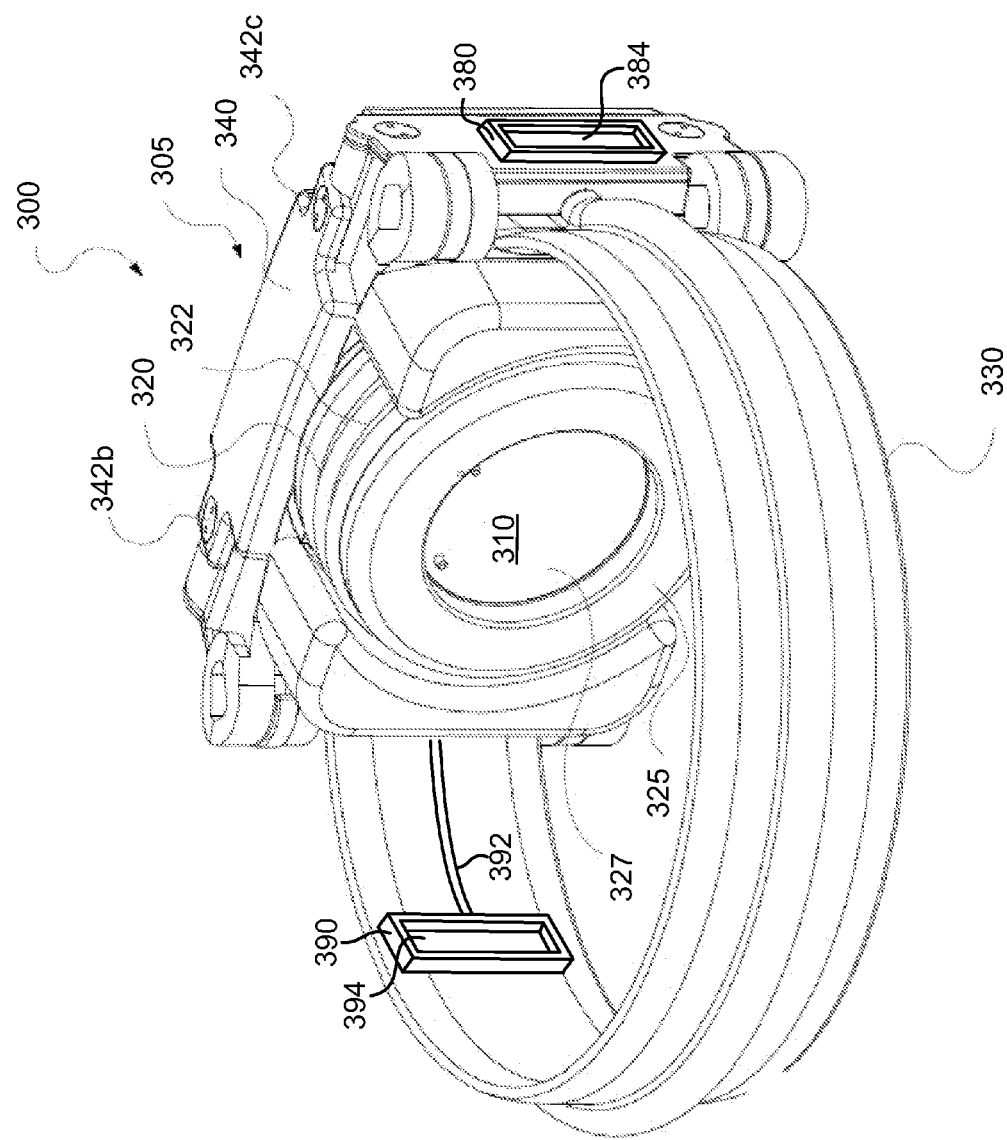
FIG. 3 depicts yet another alcohol monitoring device including dual transdermal alcohol monitors and an environmental alcohol monitor in accordance with various embodiments of the present invention.

Turning to FIG. 3, another alcohol monitoring device 300 including a first transdermal alcohol sensor 310, a second transdermal alcohol sensor 394, and an environmental alcohol sensor 384 is shown in accordance with various embodiments of the present invention. Each of transdermal alcohol sensor 310, transdermal alcohol sensor 394 and environmental alcohol sensor 384 are operable to detect the presence of alcohol in a gas such as air. In some embodiments of the present invention, transdermal alcohol sensor 310, transdermal alcohol sensor 394, and environmental alcohol sensor 384 may be the same type of sensor displaced some distance to perform a differential measurement, or may be implemented using different types of sensors. In one particular embodiment of the present invention, all of transdermal alcohol sensor 310, transdermal alcohol sensor 394 and environmental alcohol sensor 384 may include may include a fuel cell based on PEM sensor technology available from Giner Inc. of Newton, Mass., or any other alcohol detection sensor known in the art. The monitoring circuitry may include location monitoring circuitry as is known in the art, or other monitoring circuitry used to determine attributes and/or location of a monitored individual. Transdermal alcohol sensor 394 is surrounded by a housing 380, and environmental alcohol sensor 384 is surrounded by a housing 380.

In addition, alcohol monitoring device 300 may include location monitoring circuitry and/or data transmission circuitry. The location monitoring circuitry may include, but is not limited to, global position system locating circuitry. The data transmission circuitry may include, but is not limited to, transmission and/or reception circuitry as is known in the art for transmitting information from alcohol monitoring device 300, and receiving information at alcohol monitoring device 300. The information transmitted by alcohol monitoring device may include an indication of whether a monitored individual has been consuming alcohol and to what level the consumption has progressed, and/or current and historic location information of the subject wearing alcohol monitoring device.

In addition, alcohol monitoring device 300 may include tamper circuitry. Such tamper circuitry may include any circuitry known in the art that are capable of determining whether any interference with alcohol monitoring device 300 has occurred or is ongoing. Such interference may include, but is not limited to, blocking the alcohol sensor, interfering with the transmission of information to/from alcohol monitoring device 300, and/or cutting an attachment securing alcohol monitoring device 300 to the human subject. Such tamper sensors may include, but are not limited to, a proximity sensor that is able to determine whether alcohol monitoring device 300 is within reasonable proximity of the skin of the monitored individual. Based on the disclosure provided herein, one of ordinary skill in the art will recognize a variety of tamper sensors that may be used in conjunction with the various embodiments of the present invention. The various sensors included in alcohol measurement device 300 may include, but are not limited to, a blockage sensor indicating that no gas is being allowed to reach an included alcohol sensor, a temperature sensor, a proximity sensor indicating that alcohol measurement device is within a defined range of the monitored individual, a skin probe capable of measuring skin resistance as an indication of whether alcohol measurement device is still being worn by the monitored individual, and/or the like. Based on the disclosure provided herein, one of ordinary skill in the art will recognize a variety of other sensors that may be used in relation to different embodiments of the present invention.

The aforementioned location information, alcohol information, and/or tamper information may be transmitted to a central monitoring station where it is monitored. Based on the disclosure provided herein, one of ordinary skill in the art will recognize a variety of information that may be transmitted to/from alcohol monitoring device, a variety of uses of such information, and a variety of transmission methods and protocols that may be utilized in accordance with different embodiments of the present invention.

A body 305 is attachable to a human subject using a strap 330. Strap 330 is attachable using some sort of buckle or other connector as are known in the art. In some cases, strap 330 includes a continuity detector (not shown) imbedded therein. In one particular embodiment of the present invention, the continuity detector is an electrical conductor extending around strap 330 and making a connection in body 305. As such, when strap 330 is either unbuckled or cut, the electrical conductor is broken and the break is detected by circuitry within body 305. In other particular embodiments of the present invention, the continuity detector is a fiber optic conductor that may similarly be used to determine whether strap 330 has been unbuckled or cut. Based on the disclosure provided herein, one of ordinary skill in the art will appreciate a variety of straps and associated securing devices that may be used in accordance with different embodiments of the present invention to secure body 305 to a monitored individual. In one particular embodiment, strap 330 includes an outer case with an imbedded fiber optic continuity conductor and banding for added strength.

Body 305 includes transdermal alcohol sensor 310 that is maintained at a controlled distance from the monitored individual's skin by a dermal seal 325 and a telescoping housing 320. The combination of dermal seal 325 and telescoping housing 320 create a reasonably stable gas region 327 between alcohol sensor 310 and the monitored individual's skin. Dermal seal 325 may be, for example, a set of foam pads that are capable of creating a reasonable seal with the skin of a monitored individual, and yet are comfortable to the monitored individual. In particular instances, the foam pads are made of closed cell foam that allows for positioning and ergonomic fit. Based on the disclosure provided herein, one of ordinary skill in the art will recognize other materials that may be used to form dermal seal 325 in accordance with the various embodiments of the present invention. Telescoping housing 320 is operable to press alcohol sensor 310 near the skin of the monitored individual. Because of this, alcohol sensor 310 is maintained at a reasonably constant distance from the monitored individual's skin even when the individual is moving. This promotes better readings from alcohol sensor 310 without the need to tighten strap 330 beyond a comfortable point. As more fully described below, in one embodiment of the present invention, telescoping housing 320 includes an expandable bellows 322 that allows for movement of alcohol sensor 310 relative to body 305, and a spring (not shown) that presses transdermal alcohol sensor 310 and dermal seal 325 away from body 305 and toward the human subject's skin. In particular instances of the aforementioned embodiments, expandable bellows 322 is made of rubber, while in other instances it is formed of some type of flexible plastic. Based on the disclosure provided herein, one of ordinary skill in the art will recognize a variety of materials that may be used to create expandable bellows 322 in accordance with various embodiments of the present invention. In some embodiments of the present invention, housing 380 may be replaced with the same housing surrounding transdermal alcohol sensor 310 to limit the amount of environmental alcohol measured. Environmental alcohol sensor 384 is used to sense an alcohol concentration in the air surrounding the human subject.

Body 305 also includes a water tight compartment 340 that includes a replaceable liquid cartridge (not shown) and electronics (not shown) for operating alcohol monitoring device 300. Water tight compartment 340 is accessible by removing temper resistant screws 342. In some embodiments of the present invention, tamper resistant screws 342 may require a special tool for removal to minimize the possibility that a monitored individual will open water tight compartment 340 and attempt to interfere or otherwise control the operation of alcohol monitoring device 300. In other embodiments of the present invention, tamper resistant screws 342 are only one way devices allowing for the closure of water tight compartment 340. Opening water tight compartment 340 requires the destruction of tamper resistant screws 342. When water tight compartment 340 is to be resealed, a new pair of tamper resistant screws is required. In this way, any unauthorized opening of water tight compartment 340 will be readily apparent. In some cases, the aforementioned approach may be combined with a sensor (not shown) that indicates that water tight compartment 340 is open. Thus, when water tight compartment 340 is opened an error message may be prepared and transmitted to a central monitoring location by alcohol monitoring device 300. This would allow for detection of any tampering within a reasonable period of when the tampering occurred, and additional scrutiny of the monitored individuals behavior during that period. Information sensed by transdermal alcohol sensory 394 is transmitted to the electronics in body 305 via a communication path 392. This communication path 392 may also provide any liquid necessary to operate transdermal alcohol sensor 394 from body 305.

It should be noted that information from transdermal alcohol sensor 394, environmental alcohol sensor 384, and transdermal alcohol sensor 310 may be reported separately to a central monitoring system, or may be combined and reported as a combined indicator. Alternatively the information from one or more of transdermal alcohol sensor 394, environmental alcohol sensor 384, and transdermal alcohol sensor 310 may be reported separately to a central monitoring system, and the information may be combined and reported as a combined indicator. Based upon the disclosure provided herein, one of ordinary skill in the art will recognize a variety of combinations of reporting information including sensed data, processed data, and/or consumption indicators that may be provided from a combination of environmental alcohol sensor 394, and environmental alcohol sensor 384, and transdermal alcohol sensor 310.

Figure 4:
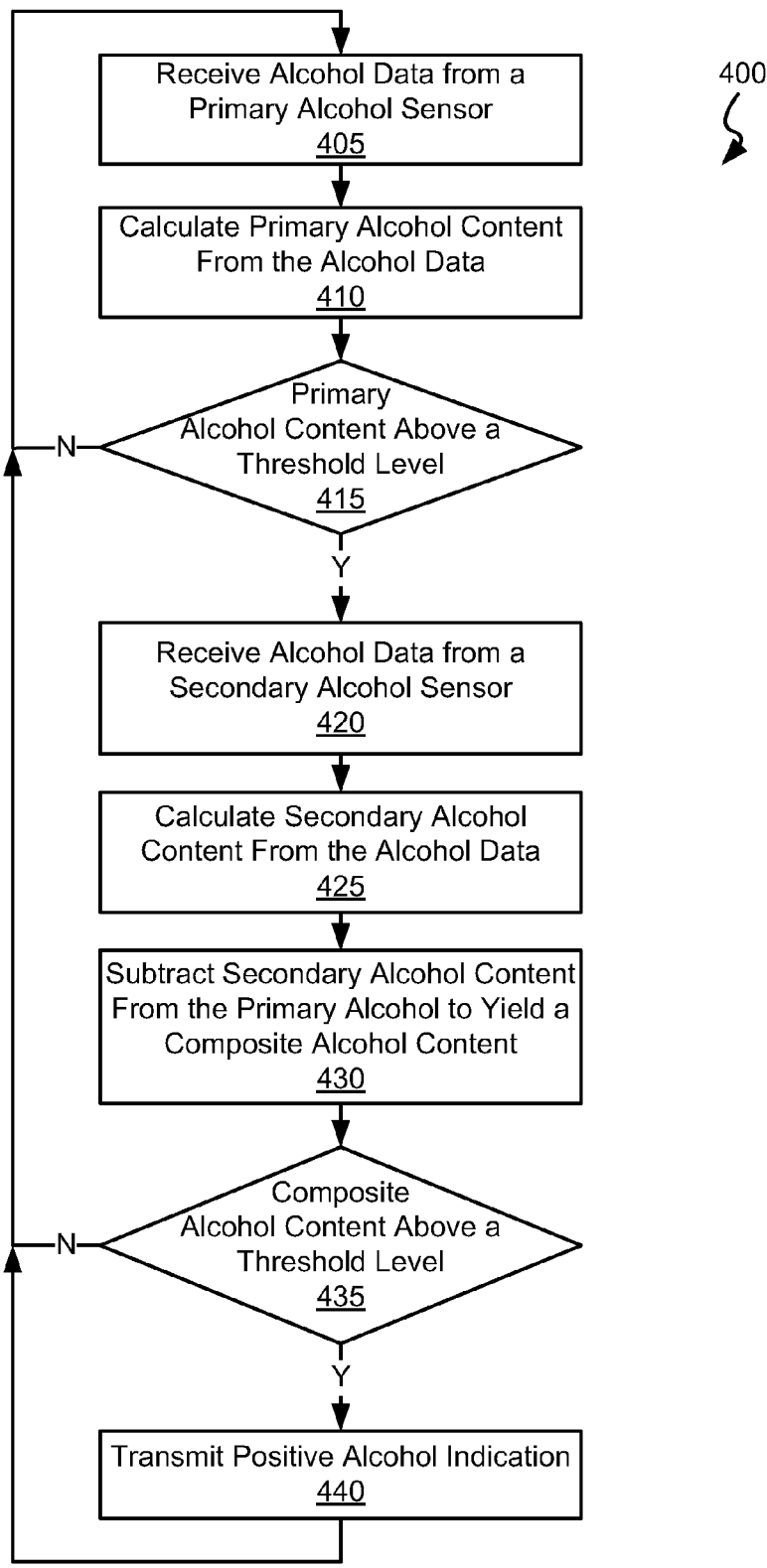
FIG. 4 is a flow diagram showing a method in accordance with some embodiments of the present invention for differentially monitoring alcohol concentrations about a monitored individual.

Turning to FIG. 4, a flow diagram 400 shows a method in accordance with some embodiments of the present invention for differentially monitoring alcohol concentrations about a monitored individual. Following flow diagram 400, alcohol data is received from a primary alcohol sensor (block 405). The primary alcohol sensor may include, but is not limited to, a fuel cell based on PEM sensor technology available from Giner Inc. of Newton, Mass., or any other alcohol detection sensor known in the art. Based upon the disclosure provided herein, one of ordinary skill in the art will recognize a variety of alcohol sensors that may be used in relation to different embodiments of the present invention. The alcohol data received from the primary alcohol sensor is used to calculate a primary alcohol content (block 410). This primary alcohol content value may be any value that quantifies an amount of alcohol sensed by the primary alcohol sensor. In one particular embodiment of the present invention, the primary alcohol content value may represent a concentration of alcohol near the primary alcohol sensor. Based upon the disclosure provided herein, one of ordinary skill in the art will recognize other representations of the primary alcohol content value that may be used in relation to different embodiments of the present invention.

It is then determined whether the primary alcohol content value exceeds a first threshold value (block 415). In some cases, the first threshold value may be programmable. Where the primary alcohol content value does not exceed the first threshold value (block 415), the process returns to block 405. Alternatively, where the primary alcohol content value exceeds the first threshold value (block 415), alcohol data is received from a secondary alcohol sensor (block 420). In some cases, the primary alcohol sensor is directed toward the skin (e.g., is pressed against the skin) of a monitored individual, and the secondary alcohol sensor is not directed toward the skin of the individual. In such a configuration, the secondary alcohol sensor readily detects alcohol in the environment around the individual and the primary alcohol sensor is directed toward sensing alcohol expired through the skin of the individual. The second sensor may include, but is not limited to, a fuel cell based on PEM sensor technology available from Giner Inc. of Newton, Mass., or any other alcohol detection sensor known in the art. Again, based upon the disclosure provided herein, one of ordinary skill in the art will recognize a variety of alcohol sensors that may be used in relation to different embodiments of the present invention. The alcohol data received from the secondary alcohol sensor is used to calculate a secondary alcohol content (block 425). This secondary alcohol content value may be any value that quantifies an amount of alcohol sensed by the secondary alcohol sensor. In one particular embodiment of the present invention, the secondary alcohol content value may represent a concentration of alcohol near the secondary alcohol sensor (e.g., an alcohol concentration in the environment around the individual. Based upon the disclosure provided herein, one of ordinary skill in the art will recognize other representations of the secondary alcohol content value that may be used in relation to different embodiments of the present invention.

A combination of the secondary alcohol content value and the primary alcohol content value are processed to yield a determination of whether the individual being monitored is likely drinking. As an example, the processing may include, but is not limited to, subtracting the secondary alcohol content value from the primary alcohol content value to yield a composite alcohol content value (block 430). The composite alcohol content value is compared against a second threshold value (block 435). In some cases, the second threshold value is programmable. Where the composite alcohol content value does not exceed the second threshold value (block 435), the process returns to block 405. Alternatively, where the composite alcohol content value exceeds the second threshold value (block 435), an indication of a likely drinking event (i.e., alcohol consumption by the monitored individual) is transmitted to a central monitoring station (block 440).

Figure 5:
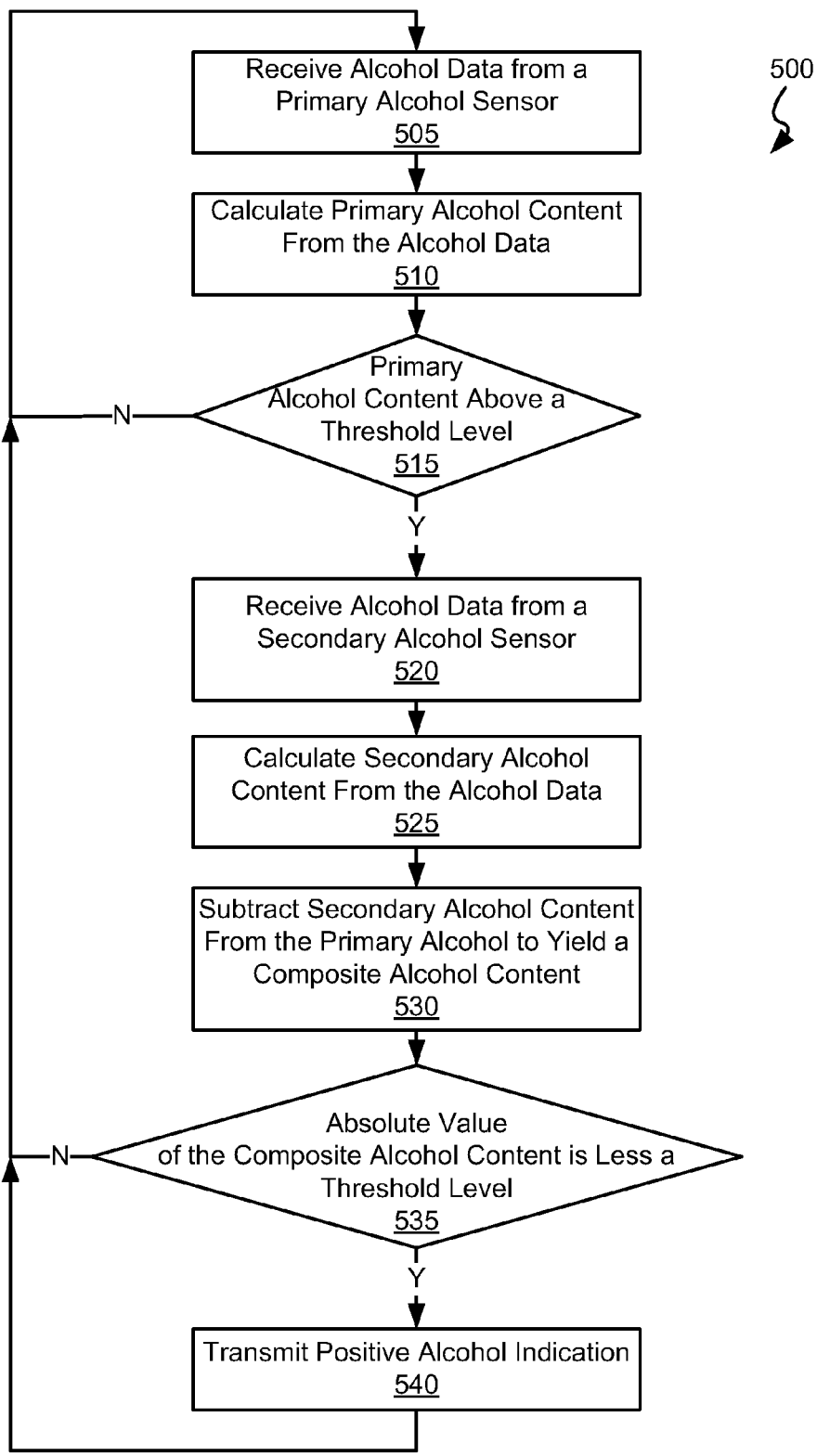
FIG. 5 is a flow diagram showing another method in accordance with some embodiments of the present invention for differentially monitoring alcohol concentrations about a monitored individual.

Turning to FIG. 5, a flow diagram 500 shows another method in accordance with some embodiments of the present invention for differentially monitoring alcohol concentrations about a monitored individual. Following flow diagram 500, alcohol data is received from a primary alcohol sensor (block 505). The primary alcohol sensor may include, but is not limited to, a fuel cell based on PEM sensor technology available from Giner Inc. of Newton, Mass., or any other alcohol detection sensor known in the art. Based upon the disclosure provided herein, one of ordinary skill in the art will recognize a variety of alcohol sensors that may be used in relation to different embodiments of the present invention. The alcohol data received from the primary alcohol sensor is used to calculate a primary alcohol content (block 510). This primary alcohol content value may be any value that quantifies an amount of alcohol sensed by the primary alcohol sensor. In one particular embodiment of the present invention, the primary alcohol content value may represent a concentration of alcohol near the primary alcohol sensor. Based upon the disclosure provided herein, one of ordinary skill in the art will recognize other representations of the primary alcohol content value that may be used in relation to different embodiments of the present invention.

It is then determined whether the primary alcohol content value exceeds a first threshold value (block 515). In some cases, the first threshold value may be programmable. Where the primary alcohol content value does not exceed the first threshold value (block 515), the process returns to block 505. Alternatively, where the primary alcohol content value exceeds the first threshold value (block 515), alcohol data is received from a secondary alcohol sensor (block 520). In some cases, the primary alcohol sensor is directed toward the skin (e.g., is pressed against the skin) as is the secondary alcohol sensor. In such a configuration, the secondary alcohol sensor primarily detects alcohol expired through the skin at one location on the monitored individual and the primary alcohol sensor primarily detects alcohol expired through the skin at another location on the monitored individual. The second sensor may include, but is not limited to, a fuel cell based on PEM sensor technology available from Giner Inc. of Newton, Mass., or any other alcohol detection sensor known in the art. Again, based upon the disclosure provided herein, one of ordinary skill in the art will recognize a variety of alcohol sensors that may be used in relation to different embodiments of the present invention. The alcohol data received from the secondary alcohol sensor is used to calculate a secondary alcohol content (block 525). This secondary alcohol content value may be any value that quantifies an amount of alcohol sensed by the secondary alcohol sensor. In one particular embodiment of the present invention, the secondary alcohol content value may represent a concentration of alcohol near the secondary alcohol sensor (e.g., an alcohol concentration in the environment around the individual). Based upon the disclosure provided herein, one of ordinary skill in the art will recognize other representations of the secondary alcohol content value that may be used in relation to different embodiments of the present invention.

A combination of the second alcohol content value and the primary alcohol content value are processed to yield a determination of whether the individual being monitored is likely drinking. As an example, the processing may include, but is not limited to, subtracting the second alcohol content value from the primary alcohol content value to yield a composite alcohol content value (block 530). An absolute value of the composite alcohol content value is compared against a second threshold value (block 535). In some cases, the second threshold value is programmable. Where the absolute value of the composite alcohol content value exceeds the second threshold value (block 535), the process returns to block 505. Alternatively, where the composite alcohol content value does not exceed the second threshold value (block 535), an indication of a likely drinking event (i.e., alcohol consumption by the monitored individual) is transmitted to a central monitoring station (block 540).

Figure 6:
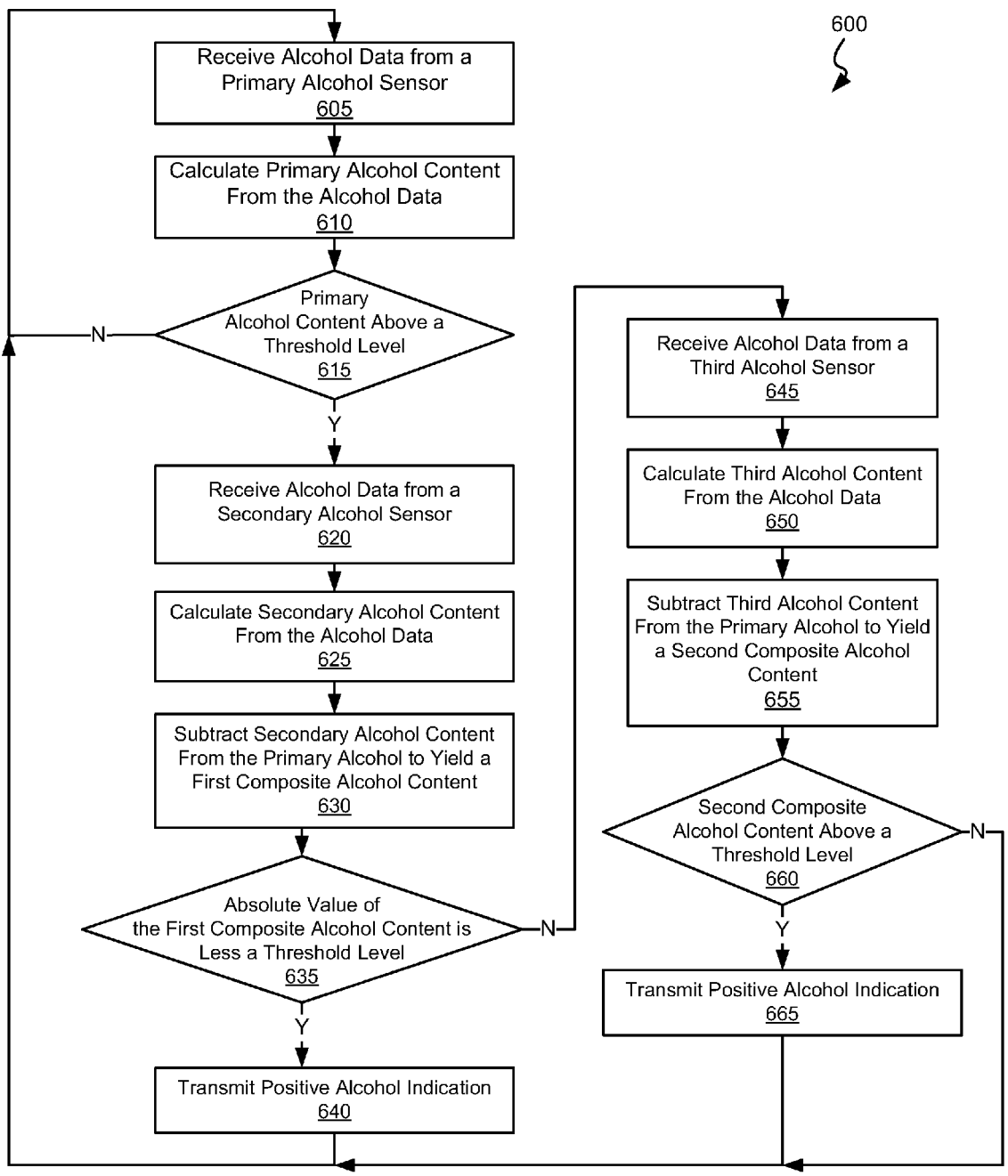
FIG. 6 is a flow diagram showing yet another method in accordance with some embodiments of the present invention for differentially monitoring alcohol concentrations about a monitored individual.

Turning to FIG. 6, a flow diagram 600 shows yet another method in accordance with some embodiments of the present invention for differentially monitoring alcohol concentrations about a monitored individual. Following flow diagram 600, alcohol data is received from a primary alcohol sensor (block 605). The primary alcohol sensor may include, but is not limited to, a fuel cell based on PEM sensor technology available from Giner Inc. of Newton, Mass., or any other alcohol detection sensor known in the art. Based upon the disclosure provided herein, one of ordinary skill in the art will recognize a variety of alcohol sensors that may be used in relation to different embodiments of the present invention. The alcohol data received from the primary alcohol sensor is used to calculate a primary alcohol content (block 610). This primary alcohol content value may be any value that quantifies an amount of alcohol sensed by the primary alcohol sensor. In one particular embodiment of the present invention, the primary alcohol content value may represent a concentration of alcohol near the primary alcohol sensor. Based upon the disclosure provided herein, one of ordinary skill in the art will recognize other representations of the primary alcohol content value that may be used in relation to different embodiments of the present invention.

It is then determined whether the primary alcohol content value exceeds a first threshold value (block 615). In some cases, the first threshold value may be programmable. Where the primary alcohol content value does not exceed the first threshold value (block 615), the process returns to block 605. Alternatively, where the primary alcohol content value exceeds the first threshold value (block 615), alcohol data is received from a secondary alcohol sensor (block 620). In some cases, the primary alcohol sensor is directed toward the skin (e.g., is pressed against the skin) as is the secondary alcohol sensor. In such a configuration, the secondary alcohol sensor primarily detects alcohol expired through the skin at one location on the monitored individual and the primary alcohol sensor primarily detects alcohol expired through the skin at another location on the monitored individual. The second sensor may include, but is not limited to, a fuel cell based on PEM sensor technology available from Giner Inc. of Newton, Mass., or any other alcohol detection sensor known in the art. Again, based upon the disclosure provided herein, one of ordinary skill in the art will recognize a variety of alcohol sensors that may be used in relation to different embodiments of the present invention. The alcohol data received from the secondary alcohol sensor is used to calculate a secondary alcohol content (block 625). This secondary alcohol content value may be any value that quantifies an amount of alcohol sensed by the secondary alcohol sensor. In one particular embodiment of the present invention, the secondary alcohol content value may represent a concentration of alcohol near the secondary alcohol sensor (e.g., an alcohol concentration in the environment around the individual. Based upon the disclosure provided herein, one of ordinary skill in the art will recognize other representations of the secondary alcohol content value that may be used in relation to different embodiments of the present invention.

A combination of the secondary alcohol content value and the primary alcohol content value are processed to yield a determination of whether the individual being monitored is likely drinking. As an example, the processing may include, but is not limited to, subtracting the secondary alcohol content value from the primary alcohol content value to yield a first composite alcohol content value (block 630). An absolute value of the first composite alcohol content value is compared against a second threshold value (block 635). In some cases, the second threshold value is programmable. Where the first composite alcohol content value does not exceed the second threshold value (block 635), an indication of a likely drinking event (i.e., alcohol consumption by the monitored individual) is transmitted to a central monitoring station (block 640).

Alternatively, where the absolute value of the first composite alcohol content value exceeds the second threshold value (block 635), alcohol data is received from a third alcohol sensor (block 645). In some cases, the third alcohol sensor is not directed toward the skin of the individual. In such a configuration, the secondary alcohol sensor readily detects alcohol in the environment around the individual and the primary alcohol sensor is directed toward sensing alcohol expired through the skin of the individual. The third sensor may include, but is not limited to, a fuel cell based on PEM sensor technology available from Giner Inc. of Newton, Mass., or any other alcohol detection sensor known in the art. Again, based upon the disclosure provided herein, one of ordinary skill in the art will recognize a variety of alcohol sensors that may be used in relation to different embodiments of the present invention. The alcohol data received from the third alcohol sensor is used to calculate a third alcohol content (block 650). This third alcohol content value may be any value that quantifies an amount of alcohol sensed by the third alcohol sensor. In one particular embodiment of the present invention, the third alcohol content value may represent a concentration of alcohol near the third alcohol sensor (e.g., an alcohol concentration in the environment around the individual. Based upon the disclosure provided herein, one of ordinary skill in the art will recognize other representations of the secondary alcohol content value that may be used in relation to different embodiments of the present invention.

A combination of the third alcohol content value and the primary alcohol content value are processed to yield a determination of whether the individual being monitored is likely drinking. As an example, the processing may include, but is not limited to, subtracting the third alcohol content value from the primary alcohol content value to yield a second composite alcohol content value (block 655). The second composite alcohol content value is compared against a third threshold value (block 660). In some cases, the third threshold value is programmable. Where the second composite alcohol content value does not exceed the second threshold value (block 660), the process returns to block 605. Alternatively, where the second composite alcohol content value exceeds the third threshold value (block 660), an indication of a likely drinking event (i.e., alcohol consumption by the monitored individual) is transmitted to a central monitoring station (block 665).

Figure 7:
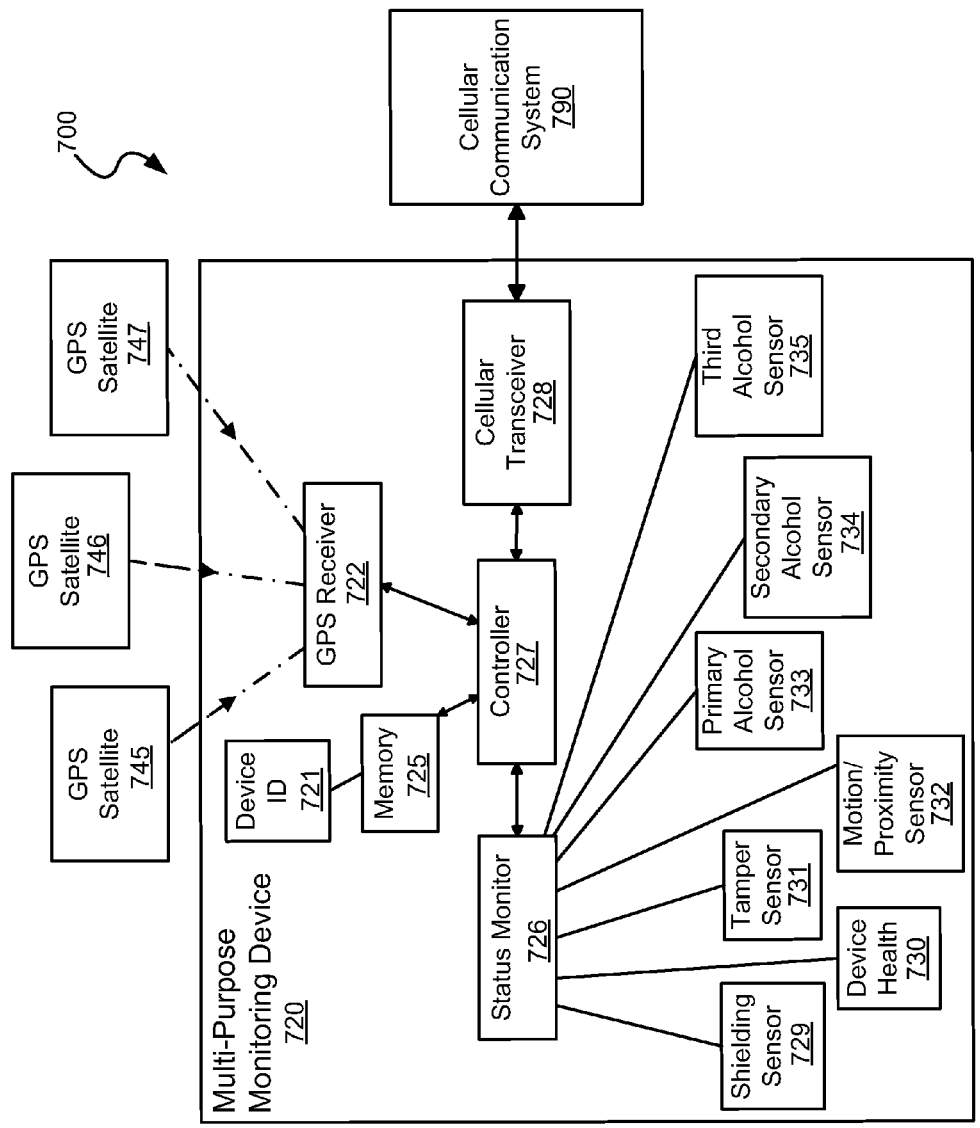
FIG. 7 depicts the block diagram of a monitoring device capable of monitoring subject location as well as alcohol usage using differential alcohol monitoring in accordance with various embodiments of the present invention.

FIG. 7 depicts the block diagram of a monitoring device 700 capable of monitoring subject location as well as alcohol usage using differential alcohol monitoring in accordance with various embodiments of the present invention. It should be noted that in some embodiments of the present invention only alcohol monitoring is done in which case the location monitoring circuitry is not needed. Monitoring device 700 includes a multi-purpose monitoring device 720. Multi-purpose monitoring device 720 may be incorporated in the electronics of the devices of FIGS. 1, 2 and 3 discussed above. As shown, multi-purpose monitoring device 720 includes a GPS receiver 722 that is capable of receiving GPS information from GPS satellites 745, 746, and 747 respectively. GPS receiver 722 is useful for determining physical locations, i.e. whenever GPS receiver 722 is powered-on, and also as long as receiving sufficient GPS satellites signal transmissions.

Multi-purpose monitoring device 720 includes a device ID 721 that may be maintained in a memory 725, and thus is accessible by a controller 727. Controller 727 is able to interact with GPS receiver 722 and memory 725 at times for storing and generating records of successively determined GPS locations. Controller 727 may be, but is not limited to, a microprocessor, microcontroller or other device known in the art that is capable of executing software or firmware instructions. Memory 725 may be any type of memory known in the art such as, for example, an EEPROM, or FLASH memory.

Controller 727 of multi-purpose monitoring device 720 at times functions in conjunction with a cellular transceiver 728 to send and receive data and signals through cellular communication system 790. This link at times is useful for passing information and/or control signals between a central monitoring system (not shown) and multi-purpose monitoring device 720. The information transmitted may include, but is not limited to, location information, alcohol information, and information about the status of multi-purpose monitoring device 720. Based on the disclosure provided herein, one of ordinary skill in the art will recognize a variety of information that may be transferred via cellular communication system 790. Additionally, one of ordinary skill in the art will recognize a variety of other communication systems that may be used either in place of or in addition to the combination of cellular transceiver 728 and cellular communication system 790.

Various embodiments of multi-purpose monitoring device 720 include a variety of sensors capable of determining the status of multi-purpose monitoring device 720, and of the individual associated therewith. For example, a status monitor 726 may include one or more of the following subcomponents: a set of shielding sensors 729 that are capable of determining whether subject device is being shielded from receiving GPS signals and/or if GPS jamming is ongoing, a set of device health indicators 730, a tamper sensor 731 capable of determining whether unauthorized access to subject device 720 has occurred or whether multi-purpose monitoring device 720 has been removed from an associated human subject, a motion/proximity sensor 732 capable of determining whether multi-purpose monitoring device 720 is moving and/or whether it is within proximity of an individual associated with multi-purpose monitoring device 720, and/or two or more alcohol sensors 733, 734, 735 such as that described herein. Based on the disclosure provided herein, one of ordinary skill in the art will recognize a variety of shielding sensors, a variety of device health transducers and indicators, a variety of tamper sensors, various different types of motion sensors, different proximity to human sensors, and various human body physical measurement sensors or transducers that may be incorporated into multi-purpose monitoring device 720 according to various different instances and/or embodiments of the present invention. In some cases, transmission of alcohol data is done at one frequency, and house arrest information is transmitted at another frequency. In one particular embodiment of the present invention, house arrest information (i.e., location information) is transmitted using a 300 MHz-320 MHz, and alcohol information is transmitted using a 902 MHz-928 MHZ band. The higher frequency band allows for transmission of substantial amounts of information, while the lower frequency band allows for transmission of smaller amounts of data. In some embodiments of the present invention, the aforementioned transmission of data to a central computer or computing system is effectuated by transmitting the aforementioned information at the stated frequencies to a fixed or mobile translation device. This fixed or mobile translation device may be, for example, a field monitoring device, as are known in the art. In turn, the fixed or mobile translation device uploads the information or an information set derived there from to the central computer. Based upon the disclosure provided herein, one of ordinary skill in the art will recognize a variety of configurations and different data transfers that may be effectuated in accordance with different embodiments of the present invention.

In conclusion, the present invention provides for novel systems, devices, and methods for monitoring alcohol consumption by human subjects. While detailed descriptions of one or more embodiments of the invention have been given above, various alternatives, modifications, and equivalents will be apparent to those skilled in the art without varying from the spirit of the invention. For example, the processing of sample information from an alcohol or other sensor may be processed local to an individual wearing the sample, remotely at a central processing location that receives the data, or in part local to the individual and in part at a central processing location depending upon the particular implementation. Therefore, the above description should not be taken as limiting the scope of the invention, which is defined by the appended claims.

What is claimed is:

1. A system for alcohol monitoring, the system comprising:
   a first alcohol sensor operable to detect a first alcohol content at a first location;
   a second alcohol sensor operable to detect a second alcohol content at a second location;
   a processor operable to process both the first alcohol content and the second alcohol content to yield a drinking indication, wherein processing both the first alcohol content and the second alcohol content includes subtracting the second alcohol content from the first alcohol content to yield a consumption indicator, and wherein the drinking indication corresponds to the consumption indication;
   wherein the first alcohol sensor and the second alcohol sensor are incorporated into a monitor device that includes a connector device, and wherein the connector device is operable to attach the monitor device to a limb of a monitored individual such that the monitor device moves with the monitored individual when the monitored individual is walking.

2. The system of claim 1, wherein the first alcohol content and the second alcohol content are reported separately to a receiving system.

3. The system of claim 1, wherein at least one of the first alcohol content and the second alcohol content are reported to the receiving system along with the consumption indicator.

4. The system of claim 1, wherein the drinking indication corresponds to alcohol consumption of the monitored individual.

5. The system of claim 1, wherein the first alcohol sensor is directed toward the skin of the monitored individual, wherein the second alcohol sensor is directed toward an environment around the monitored individual, and wherein the first location is nearer the monitored individual than the second location.

6. The system of claim 1, wherein the first alcohol sensor is directed toward the skin of the monitored individual, wherein the second alcohol sensor is directed toward the skin of the monitored individual.

7. The system of claim 6, wherein the system further comprises:
   a third alcohol sensor directed away from the skin of the monitored individual and operable to detect a third alcohol content; and
   wherein the processor is further operable to process all of the first alcohol content the second alcohol content, and the third alcohol content to yield the drinking indication.

8. The system of claim 7, wherein processing all of the first alcohol content, the second alcohol content, and the third alcohol content to yield the drinking indication includes:
   subtracting the second alcohol content from the first alcohol content to yield a first composite alcohol content; and
   subtracting the third alcohol content from the first alcohol content to yield a second composite alcohol content.

9. The system of claim 1, wherein the monitor device further comprises:
   a location monitor circuit operable to monitor a location of the monitored individual.

10. The system of claim 1, wherein the monitor device further comprises:
    a tamper monitor circuit operable to monitor a tampering of the monitor device.

11. The system of claim 1, wherein the connector device is a strap operable to attach the monitor device to the monitored individual.

12. The system of claim 1, wherein processing of both the first alcohol content and the second alcohol content to yield the drinking indication includes:
   subtracting the second alcohol content from the first alcohol content to yield a composite alcohol content; and
   comparing the composite alcohol content with a threshold value to yield the drinking indication.

13. The system of claim 1, wherein the system further comprises:
   a communication circuit operable to communicate the drinking indication to a recipient.

14. The system of claim 1, wherein the first alcohol sensor and the second alcohol sensor are the same type of alcohol sensors.

15. The system of claim 1, wherein the first alcohol sensor and the second alcohol sensor detect the same type of interferents.

16. A method for monitoring alcohol consumption by a monitored individual, the method comprising:
   receiving a first alcohol content value derived from a first alcohol sensor disposed in relation to a monitored individual;
   receiving a second alcohol content value derived from a second alcohol sensor disposed in relation to the monitored individual;
   determining alcohol consumption by the monitored individual using both the first alcohol content value and the second alcohol content value, wherein determining the alcohol consumption includes subtracting the second alcohol content value from the first alcohol content value to yield a consumption indicator;
   wherein the first alcohol sensor and the second alcohol sensor are associated with a monitor device; and
   attaching the monitor device to a limb of the monitored individual such that the monitor device moves with the monitored individual when the monitored individual is walking.

17. The method of claim 16, wherein the first alcohol sensor is directed toward the skin of the monitored individual, wherein the second alcohol sensor is directed toward an environment around the monitored individual, and wherein the first location is nearer the monitored individual than the second location.

18. The method of claim 16, wherein the first alcohol sensor is directed toward the skin of the monitored individual, wherein the second alcohol sensor is directed toward the skin of the monitored individual.

19. The method of claim 18, wherein the monitoring device further comprises:
   a third alcohol sensor directed away from the skin of the monitored individual and operable to detect a third alcohol content; and
   wherein determining alcohol consumption by the monitored individual uses all of the first alcohol content value, the second alcohol content value, and the third alcohol content value.

20. The method of claim 16, wherein the method further comprises:
   monitoring a location of the monitored individual.

21. The method of claim 16, wherein the method further comprises:
   reporting the first alcohol content value and the second alcohol content value to a central monitor via a communication link.

22. The method of claim 16, wherein the method further comprises:
   reporting the drinking indication to a central monitor via a communication link, wherein the drinking indication is generated based at least in part on the consumption indicator.

* * * * *